US007941886B2

(12) United States Patent
Chenvainu et al.

(10) Patent No.: US 7,941,886 B2
(45) Date of Patent: May 17, 2011

(54) TOOTHBRUSHES

(75) Inventors: Alexander T. Chenvainu, Sudbury, MA (US); Thomas A. Christman, Lexington, MA (US)

(73) Assignee: Braun GmbH, Kronberg (DE)

( * ) Notice: Subject to any disclaimer, the term of this patent is extended or adjusted under 35 U.S.C. 154(b) by 0 days.

(21) Appl. No.: 10/666,497

(22) Filed: Sep. 19, 2003

(65) Prior Publication Data

US 2005/0060822 A1 Mar. 24, 2005

(51) Int. Cl.
*A61C 17/22* (2006.01)
(52) U.S. Cl. .......................................... 15/22.4; 15/22.1
(58) Field of Classification Search .................. 15/22.1, 15/22.2, 28, 167.1, 176.1; D4/127
See application file for complete search history.

(56) References Cited

U.S. PATENT DOCUMENTS

| | | |
|---|---|---|
| 75,421 A | 3/1868 | Hayward |
| 116,346 A | 6/1871 | O'Brian |
| 301,644 A | 7/1884 | Thompson |
| 429,839 A | 6/1890 | Beissbarth |
| 601,405 A | 3/1898 | Shepherd |
| D28,990 S | 7/1898 | Cumming |
| 819,444 A | 5/1906 | Monroe |
| 907,842 A | 12/1908 | Meuzies |
| 1,022,920 A | 4/1912 | Anderson |
| 1,063,523 A | 6/1913 | Farrar |
| 1,091,090 A | 3/1914 | Tacail |
| 1,128,139 A | 2/1915 | Hoffman |
| 1,142,698 A | 6/1915 | Grove et al. |
| 1,153,409 A | 9/1915 | Wheeler |
| 1,172,109 A | 2/1916 | Cammack |
| 1,188,134 A | 6/1916 | Arbat |
| 1,191,556 A | 7/1916 | Blake |
| 1,251,250 A | 12/1917 | Libby |
| 1,268,544 A | 6/1918 | Cates |
| 1,297,272 A | 3/1919 | Strang et al. |
| 1,323,042 A | 11/1919 | Gardner |
| 1,334,911 A | 3/1920 | Lampkin |
| 1,358,195 A | 11/1920 | Gabryszek |
| 1,526,267 A | 2/1925 | Dessau |
| 1,544,404 A | 6/1925 | Hummel |
| 1,588,785 A | 6/1926 | Van Sant |
| 1,593,763 A | 7/1926 | Henderson |
| 1,598,224 A | 8/1926 | Van Sant |
| 1,673,638 A | 6/1928 | Peterson |
| 1,693,229 A | 11/1928 | Felmar |
| 1,698,128 A | 1/1929 | Funk |

(Continued)

FOREIGN PATENT DOCUMENTS

AU 4469693 6/1994

(Continued)

OTHER PUBLICATIONS

Colgate Actibrush Active Cleaning Tip.

(Continued)

*Primary Examiner* — Laura C Guidotti
(74) *Attorney, Agent, or Firm* — John P. Colbert; George H. Leal

(57) ABSTRACT

Toothbrush heads, e.g., for power toothbrushes, are provided. The toothbrush heads include a support member and a plurality of bristles or tufts of bristles extending from the support member, the bristles or bristle tufts having different lengths. The contour of the bristles may be selected to allow substantially all of the bristles to contact the dentition during brushing.

16 Claims, 10 Drawing Sheets

U.S. PATENT DOCUMENTS

| | | | |
|---|---|---|---|
| 1,704,564 A | 3/1929 | Friedland | |
| 1,720,017 A | 7/1929 | Touchstone | |
| 1,753,290 A | 4/1930 | Graves | |
| 1,758,632 A | 5/1930 | Wagner | |
| 1,764,130 A | 6/1930 | Vardeman | |
| 1,796,893 A | 3/1931 | McVeigh | |
| 1,797,946 A | 3/1931 | Eichel | |
| 1,863,389 A | 5/1931 | Anderson | |
| 1,832,519 A | 11/1931 | Wheat et al. | |
| 1,840,246 A | 1/1932 | Newman | |
| 1,852,480 A | 4/1932 | Ruetz | |
| 1,872,832 A | 8/1932 | Silverberg | |
| 1,897,726 A | 2/1933 | Hillyard | |
| 1,907,286 A | 5/1933 | Chott | |
| 1,908,510 A | 5/1933 | Dodson | |
| 1,910,414 A | 5/1933 | Varga | |
| 1,924,152 A | 8/1933 | Coney et al. | |
| 1,943,225 A | 1/1934 | McIntyre | 15/167 |
| 1,963,389 A | 6/1934 | Vardeman | |
| 1,993,662 A | 3/1935 | Green | |
| 2,042,239 A | 5/1936 | Planding | |
| 2,155,473 A | 9/1936 | Coleman | |
| 2,059,914 A | 11/1936 | Rosenberg | |
| 2,088,839 A | 8/1937 | Coney et al. | |
| 2,093,007 A | 9/1937 | Chott | |
| 2,117,174 A | 5/1938 | Jones | |
| 2,129,082 A | 9/1938 | Byrer | |
| 2,139,245 A | 12/1938 | Ogden | |
| 2,154,846 A | 4/1939 | Heymann et al. | |
| 2,164,219 A | 6/1939 | McGerry | |
| 2,172,624 A | 9/1939 | Gabriel et al. | |
| 2,175,975 A | 10/1939 | Steiner | |
| 2,176,309 A | 10/1939 | Love et al. | |
| 2,189,175 A | 2/1940 | Jackson | |
| 2,139,249 A | 3/1940 | Flanders et al. | |
| 2,206,726 A | 7/1940 | Lasater | |
| 2,219,753 A | 10/1940 | Seguin | |
| 2,220,053 A | 10/1940 | Pruner | |
| 2,225,331 A | 12/1940 | Campbell | |
| 2,226,145 A | 12/1940 | Smith | |
| 2,238,603 A | 4/1941 | Runnels | |
| 2,244,699 A | 6/1941 | Hosey | |
| 2,246,867 A | 6/1941 | Thomas et al. | |
| 2,263,802 A | 11/1941 | Grusin | 15/110 |
| 2,266,195 A | 12/1941 | Lay | |
| 2,279,355 A | 4/1942 | Wilensky | |
| 2,312,828 A | 3/1943 | Adamsson | |
| 2,326,632 A | 8/1943 | Friedman | |
| 2,328,998 A | 9/1943 | Radford | |
| 2,364,205 A | 12/1944 | Fuller | |
| 2,443,461 A | 6/1948 | Kempster | |
| 2,486,203 A | 10/1949 | Pieper | |
| 2,486,847 A | 11/1949 | Hokett | 401/273 |
| 2,556,691 A | 6/1951 | Harshbarger | |
| 2,583,886 A | 1/1952 | Schlegel | |
| 2,584,735 A | 2/1952 | Pancoast | |
| 2,604,649 A | 7/1952 | Stephenson et al. | 15/185 |
| 2,622,259 A | 12/1952 | Chauvin | 15/167 |
| 2,625,697 A | 1/1953 | Cyser | 15/22 |
| 2,628,377 A | 2/1953 | Cockriel | |
| 2,637,870 A | 5/1953 | Cohen | 15/188 |
| 2,653,598 A | 9/1953 | Torino | |
| 2,655,674 A | 10/1953 | Grover | |
| 2,655,675 A | 10/1953 | Grover | |
| 2,655,676 A | 10/1953 | Grover | |
| 2,702,914 A | 3/1955 | Kittle et al. | |
| 2,832,088 A | 4/1958 | Peilet et al. | |
| 2,882,544 A | 4/1959 | Hadidian | 15/167.1 |
| 2,935,755 A | 5/1960 | Leira | 15/167.1 |
| 3,007,441 A | 11/1961 | Eyer | |
| 3,016,554 A | 1/1962 | Peterson | |
| 3,050,072 A | 8/1962 | Diener | |
| 3,082,457 A | 3/1963 | Lucibello et al. | |
| 3,103,027 A | 9/1963 | Birch | |
| 3,110,918 A | 11/1963 | Tate | 15/167.1 |
| 3,128,487 A | 4/1964 | Vallis | |
| 3,129,449 A | 4/1964 | Cyzer | 15/28 |
| 3,133,546 A | 5/1964 | Dent | |
| 3,159,859 A | 12/1964 | Rasmussen | |
| 3,177,509 A | 4/1965 | Cyzer | |
| 3,195,537 A | 7/1965 | Blasi | 128/56 |
| 3,196,299 A * | 7/1965 | Kott | 310/81 |
| 3,230,562 A | 1/1966 | Birch | 15/110 |
| 3,258,805 A | 7/1966 | Rossnan | |
| 3,261,354 A | 7/1966 | Shpuntoff | 128/173 |
| 3,295,156 A | 1/1967 | Brant | |
| 3,302,230 A | 2/1967 | Poppelman | |
| 3,316,576 A * | 5/1967 | Urbush | 15/22.1 |
| 3,327,339 A | 6/1967 | Lemelson | |
| 3,359,588 A | 12/1967 | Kobler | 15/110 |
| 3,386,118 A | 6/1968 | Morioku et al. | |
| 3,398,421 A | 8/1968 | Rashbaum | |
| 3,403,070 A | 9/1968 | Lewis, Jr. | |
| 3,411,979 A | 11/1968 | Lewis | |
| RE26,688 E | 10/1969 | Lemelson | |
| 3,491,396 A | 1/1970 | Eannarino et al. | |
| 3,553,759 A | 1/1971 | Kramer et al. | |
| 3,613,143 A | 10/1971 | Muhler et al. | |
| 3,619,845 A | 11/1971 | Partridge et al. | 15/117 |
| 3,683,442 A | 8/1972 | Holly | |
| 3,742,549 A | 7/1973 | Scopp et al. | 15/167 R |
| 3,742,608 A | 7/1973 | Jones | |
| 3,804,011 A | 4/1974 | Zimmer | 101/120 |
| 3,903,906 A | 9/1975 | Collis | |
| 3,939,522 A | 2/1976 | Shimizu | 15/244 R |
| 3,977,084 A | 8/1976 | Sloan | 32/59 |
| 3,978,852 A | 9/1976 | Annoni | 128/62 A |
| 3,984,890 A | 10/1976 | Collis | |
| 4,033,008 A | 7/1977 | Warren et al. | |
| 4,081,877 A | 4/1978 | Vitale | 15/188 |
| 4,114,222 A | 9/1978 | Serediuk | 15/186 |
| 4,115,893 A | 9/1978 | Nakata et al. | |
| 4,128,910 A | 12/1978 | Nakata et al. | 15/110 |
| 4,156,620 A | 5/1979 | Clemens | |
| 4,167,794 A | 9/1979 | Pomeroy | |
| 4,202,361 A | 5/1980 | Bills | |
| 4,263,691 A | 4/1981 | Pakarnseree | 15/159 A |
| 4,268,933 A | 5/1981 | Papas | |
| 4,277,862 A | 7/1981 | Weideman | 15/110 |
| 4,288,883 A | 9/1981 | Dolinsky | 15/110 |
| 4,317,463 A | 3/1982 | Massetti | |
| 4,356,585 A | 11/1982 | Protell et al. | |
| 4,373,541 A | 2/1983 | Nishioka | |
| 4,391,951 A | 7/1983 | Scheetz | |
| 4,399,582 A * | 8/1983 | Ernest et al. | 15/176.4 |
| 4,403,623 A | 9/1983 | Mark | |
| 4,409,701 A | 10/1983 | Perches | |
| 4,428,091 A | 1/1984 | Janssen | |
| 4,429,434 A | 2/1984 | Sung-shan | |
| 4,472,853 A | 9/1984 | Rauch | 15/167 R |
| 4,476,280 A | 10/1984 | Poppe et al. | |
| 4,480,351 A | 11/1984 | Koffler | |
| 4,517,701 A | 5/1985 | Stanford, Jr. | |
| 4,519,111 A | 5/1985 | Cavazza | 15/167 R |
| 4,525,531 A | 6/1985 | Zukosky et al. | |
| 4,534,081 A | 8/1985 | Spademan | |
| 4,545,087 A | 10/1985 | Nahum | |
| 4,573,920 A | 3/1986 | D'Argembeau | |
| 4,585,416 A | 4/1986 | DeNiro et al. | 433/140 |
| 4,603,166 A | 7/1986 | DeNiro et al. | |
| 4,616,064 A | 10/1986 | Zukosky et al. | |
| 4,617,342 A | 10/1986 | Poppe et al. | |
| 4,617,694 A | 10/1986 | Bori | |
| 4,619,009 A | 10/1986 | Rosenstatter | 15/29 |
| 4,623,495 A | 11/1986 | Degoix et al. | |
| 4,633,542 A | 1/1987 | Taravel | 15/167.1 |
| 4,654,922 A | 4/1987 | Chen | |
| 4,672,706 A | 6/1987 | Hill | |
| 4,691,405 A | 9/1987 | Reed | |
| 4,694,844 A | 9/1987 | Berl et al. | 15/167.1 |
| 4,706,322 A | 11/1987 | Nicolas | |
| 4,739,532 A | 4/1988 | Behrend | 15/28 |
| 4,744,350 A | 5/1988 | Sato | |
| 4,776,054 A | 10/1988 | Rauch | 15/167.1 |
| 4,783,874 A | 11/1988 | Perches et al. | |
| 4,802,255 A | 2/1989 | Breuer et al. | |
| 4,827,551 A | 5/1989 | Maser et al. | 15/24 |

| | | | | | | |
|---|---|---|---|---|---|---|
| 4,833,194 A | 5/1989 | Kuan et al. | | 5,799,353 A | 9/1998 | Oishi et al. ............... 15/167.1 |
| 4,751,761 A | 6/1989 | Stoy et al. | | 5,799,354 A | 9/1998 | Amir ............................ 15/167.1 |
| 4,845,795 A | 7/1989 | Linderborg | | 5,802,656 A | 9/1998 | Dawson et al. ............... 15/110 |
| 4,852,202 A | 8/1989 | Ledwitz | | 5,810,856 A | 9/1998 | Tveras ........................ 606/161 |
| 4,882,803 A | 11/1989 | Rogers et al. | | 5,813,079 A | 9/1998 | Halm .......................... 15/167.1 |
| 4,892,698 A | 1/1990 | Weihrauch | | 5,823,633 A | 10/1998 | Weihrauch |
| 4,894,880 A | 1/1990 | Aznavoorian | | D401,414 S | 11/1998 | Vrignaud |
| 4,913,133 A | 4/1990 | Tichy | | 5,836,033 A | 11/1998 | Berge .......................... 15/110 |
| 4,972,782 A | 12/1990 | Weihrauch | | 5,839,148 A | 11/1998 | Volpenhein ............... 15/167.1 |
| 4,979,256 A | 12/1990 | Branford | | 5,842,249 A | 12/1998 | Sato |
| 4,989,287 A | 2/1991 | Scherer | | 5,864,915 A | 2/1999 | Ra |
| 4,991,249 A | 2/1991 | Suroff | | 5,881,425 A * | 3/1999 | Hudson et al. ............... 15/167.1 |
| 5,020,179 A | 6/1991 | Scherer | | 5,885,363 A | 3/1999 | Nakamura ..................... 134/6 |
| 5,021,475 A | 6/1991 | Isayev | | 5,896,614 A | 4/1999 | Flewitt ....................... 15/167.1 |
| 5,034,450 A | 7/1991 | Betz et al. | | 5,930,860 A | 8/1999 | Shipp .......................... 15/110 |
| 5,040,260 A | 8/1991 | Michaels ..................... 15/167.1 | | 5,930,861 A * | 8/1999 | White ........................ 15/167.1 |
| 5,070,567 A | 12/1991 | Holland ........................... 15/28 | | 5,946,759 A | 9/1999 | Cann |
| 5,101,530 A | 4/1992 | Hansen et al. ................... 15/245 | | 5,946,789 A | 9/1999 | Cann |
| D325,821 S | 5/1992 | Schwartz | | 5,970,564 A | 10/1999 | Inns et al. ....................... 15/201 |
| 5,114,214 A | 5/1992 | Barman | | 5,974,619 A | 11/1999 | Weihrauch |
| 5,120,225 A | 6/1992 | Amit | | 5,987,681 A | 11/1999 | Hahn et al. |
| D328,807 S | 8/1992 | Millar ........................... D32/41 | | 5,987,688 A | 11/1999 | Roberts et al. ............... 15/167.1 |
| 5,137,039 A | 8/1992 | Klinkhammer ............... 132/308 | | 5,991,959 A | 11/1999 | Raven et al. ..................... 15/201 |
| 5,142,724 A | 9/1992 | Park | | 6,018,840 A | 2/2000 | Guay et al. |
| 5,165,131 A | 11/1992 | Staar | | 6,021,538 A * | 2/2000 | Kressner et al. ................... 15/28 |
| 5,184,368 A | 2/1993 | Holland | | 6,035,476 A | 3/2000 | Underwood et al. |
| 5,186,627 A | 2/1993 | Amit et al. | | 6,041,467 A | 3/2000 | Roberts et al. ............... 15/167.1 |
| 5,212,848 A | 5/1993 | Geyer ........................... 15/401 | | 6,058,541 A | 5/2000 | Masterman et al. ............... 15/28 |
| 5,226,197 A | 7/1993 | Nack et al. | | 6,067,684 A | 5/2000 | Kweon ........................ 15/167.1 |
| 5,228,166 A | 7/1993 | Harris et al. | | 6,088,870 A | 7/2000 | Hohlbein |
| 5,249,327 A | 10/1993 | Hing | | 6,099,309 A | 8/2000 | Cardarelli ..................... 433/125 |
| 5,269,038 A | 12/1993 | Bradley ....................... 15/167.1 | | 6,112,361 A | 9/2000 | Brice |
| 5,271,682 A | 12/1993 | Realdon ......................... 401/37 | | 6,138,310 A | 11/2000 | Azagury |
| D345,054 S | 3/1994 | Spence, Jr. | | 6,151,745 A | 11/2000 | Roberts et al. |
| 5,291,878 A | 3/1994 | Lombardo et al. | | D434,906 S | 12/2000 | Beals et al. ..................... D4/104 |
| 5,305,489 A | 4/1994 | Lage ........................... 15/167.1 | | 6,161,245 A | 12/2000 | Weihrauch |
| 5,313,909 A | 5/1994 | Tseng et al. | | 6,178,582 B1 | 1/2001 | Halm |
| 5,315,731 A * | 5/1994 | Millar ........................ 15/167.1 | | 6,199,242 B1 | 3/2001 | Masterman et al. |
| 5,318,352 A | 6/1994 | Hollan | | 6,202,241 B1 | 3/2001 | Hassell et al. |
| 5,321,726 A | 6/1994 | Kafadar | | D440,048 S | 4/2001 | Beals et al. |
| 5,325,560 A | 7/1994 | Pavone et al. | | 6,209,164 B1 | 4/2001 | Sato |
| 5,334,646 A | 8/1994 | Chen | | 6,230,717 B1 | 5/2001 | Marx et al. ..................... 132/308 |
| 5,342,284 A | 8/1994 | Lemon et al. | | 6,237,178 B1 | 5/2001 | Krammer et al. ............... 15/22.1 |
| D350,851 S | 9/1994 | Spence, Jr. | | D443,985 S | 6/2001 | Beals et al. ..................... D4/104 |
| 5,347,676 A | 9/1994 | Saitoh .......................... 15/245 | | 6,253,404 B1 | 7/2001 | Boland et al. |
| 5,349,716 A | 9/1994 | Millar ........................... 15/245 | | 0,013,151 A1 | 8/2001 | Gelder et al. |
| 5,350,248 A | 9/1994 | Chen | | D446,941 S | 8/2001 | Kraemer ...................... D4/111 |
| 5,357,644 A | 10/1994 | Theriault ...................... 15/22.1 | | 6,286,173 B1 | 9/2001 | Briones |
| 5,392,483 A | 2/1995 | Heinzelman et al. ........ 15/167.1 | | 6,290,302 B1 | 9/2001 | Boucherie |
| 5,398,366 A | 3/1995 | Bradley ....................... 15/167.1 | | 6,298,513 B1 | 10/2001 | Beal at el. |
| 5,407,254 A | 4/1995 | Hegemann | | 6,308,367 B1 | 10/2001 | Beals et al. |
| 5,421,726 A | 6/1995 | Okada | | 6,311,358 B1 | 11/2001 | Soetewey et al. ............... 15/110 |
| 5,435,032 A | 7/1995 | McDougall ................... 15/22.1 | | 6,363,565 B1 * | 4/2002 | Paffrath ........................... 15/28 |
| 5,458,400 A | 10/1995 | Meyer | | D457,000 S | 5/2002 | Lim |
| 5,476,384 A | 12/1995 | Giuliani et al. | | 6,389,634 B1 | 5/2002 | Devlin et al. .................... 15/110 |
| 5,524,319 A | 6/1996 | Avidor | | 6,391,445 B1 | 5/2002 | Weihrauch |
| 5,528,786 A | 6/1996 | Porat et al. ..................... 15/22.1 | | 6,405,401 B1 | 6/2002 | Hellerud et al. |
| 5,535,474 A | 7/1996 | Salazar | | D459,892 S | 7/2002 | Eliav et al. .................... D4/101 |
| 5,539,949 A | 7/1996 | Stanton ........................... 15/121 | | 6,421,865 B1 | 7/2002 | McDougall |
| 5,546,626 A | 8/1996 | Chung | | 6,421,867 B1 * | 7/2002 | Weihrauch ........................ 15/28 |
| 5,584,690 A | 12/1996 | Maassarani ................... 433/125 | | 6,446,295 B1 | 9/2002 | Calabrese ........................ 15/28 |
| 5,590,434 A | 1/1997 | Imai | | 6,453,497 B1 | 9/2002 | Chiang et al. |
| 5,593,213 A | 1/1997 | Meessmann | | 6,463,618 B1 | 10/2002 | Zimmer ........................ 15/110 |
| 5,604,951 A * | 2/1997 | Shipp ......................... 15/167.1 | | 6,477,729 B1 | 11/2002 | Ben-Ari |
| 5,623,746 A | 4/1997 | Ichiro | | 6,513,182 B1 | 2/2003 | Calabrese et al. |
| 5,628,082 A | 5/1997 | Moskovich ................... 15/110 | | 6,553,604 B1 | 4/2003 | Braun et al. ................... 15/167.1 |
| 5,651,157 A | 7/1997 | Hahn | | 6,564,416 B1 | 5/2003 | Claire et al. ................... 15/167.1 |
| 5,652,990 A * | 8/1997 | Driesen et al. ..................... 15/28 | | 6,571,417 B1 | 6/2003 | Gavney, Jr. et al. |
| 5,658,148 A | 8/1997 | Neuberger et al. | | 6,654,979 B2 | 12/2003 | Calabrese ........................ 15/28 |
| 5,660,546 A | 8/1997 | Shafer | | 6,658,688 B2 | 12/2003 | Gavney, Jr. .................... 15/117 |
| 5,678,275 A | 10/1997 | Derfner | | 6,701,565 B2 | 3/2004 | Hafemann |
| D386,617 S | 11/1997 | Shyu | | 6,725,490 B2 | 4/2004 | Blaustein et al. |
| 5,706,542 A | 1/1998 | Okada | | 6,725,493 B2 | 4/2004 | Calabrese et al. ............... 15/110 |
| 5,709,751 A | 1/1998 | van der Meulen ............ 118/413 | | 6,776,597 B2 | 8/2004 | Buhler |
| 5,722,106 A | 3/1998 | Masterman et al. | | 6,807,703 B2 | 10/2004 | Van Gelder et al. |
| 5,723,543 A | 3/1998 | Modic | | 6,813,793 B2 | 11/2004 | Eliav ............................ 15/22.2 |
| 5,735,011 A | 4/1998 | Asher .......................... 15/167.1 | | 6,820,300 B2 | 11/2004 | Gavney, Jr. .................... 15/117 |
| 5,778,474 A | 7/1998 | Shek | | 6,826,797 B1 | 12/2004 | Chenvainu et al. |
| 5,791,007 A | 8/1998 | Tsai | | 6,859,969 B2 | 3/2005 | Gavney, Jr. et al. ............... 15/117 |

| | | | | | | |
|---|---|---|---|---|---|---|
| 6,889,401 B2 | 5/2005 | Fattori et al. | | CH | 103 194 | 1/1924 |
| 6,892,412 B2 | 5/2005 | Gatzemeyer et al. | | CH | 169 312 | 5/1934 |
| 6,892,413 B2 | 5/2005 | Blaustein et al. | | CH | 609238 | 2/1979 |
| 6,918,154 B2 | 7/2005 | Ben-Ari | | CN | 2119280 U | 10/1992 |
| 6,931,688 B2 | 8/2005 | Moskovich et al. | | CN | 220092 | 2/1994 |
| 6,938,294 B2 | 9/2005 | Fattori et al. | | CN | 2314644 Y | 4/1999 |
| 6,983,507 B2 | 1/2006 | McDougall | | CN | 1314133 | 9/2001 |
| 6,988,777 B2 | 1/2006 | Pfenniger et al. | | CN | 1328425 | 12/2001 |
| 6,993,804 B1 | 2/2006 | Braun et al. | | CN | 1359272 | 7/2002 |
| 6,993,807 B2 | 2/2006 | Braun et al. | | DE | 558 852 | 9/1932 |
| 7,008,225 B2 | 3/2006 | Ito et al. | | DE | 571724 | 3/1933 |
| 7,160,508 B2 | 1/2007 | Lee | | DE | 813 990 | 7/1949 |
| 7,222,381 B2 | 5/2007 | Kraemer | | DE | 1112966 | 8/1961 |
| 7,225,494 B2 | 6/2007 | Chan | | DE | 1 883 020 | 11/1963 |
| 7,251,849 B2 | 8/2007 | Moskovich et al. | | DE | 1 210 409 | 2/1966 |
| 7,392,562 B2 | 7/2008 | Boland et al. | | DE | 7343826 U | 11/1974 |
| 7,494,566 B2 | 2/2009 | Carroll et al. | | DE | 75 33 143 U | 2/1976 |
| 2001/0003600 A1 | 6/2001 | Guay | 427/2.29 | DE | 25 00132 | 7/1976 |
| 2001/0007161 A1 | 7/2001 | Masterman et al. | | DE | 25 46 712 A | 4/1977 |
| 2001/0020314 A1 | 9/2001 | Calabrese | | DE | 25 46 712 A1 | 4/1977 |
| 2002/0004964 A1 | 1/2002 | Luchino et al. | | DE | 3621815 | 10/1978 |
| 2002/0084550 A1 | 7/2002 | Roberts et al. | | DE | 2 402 785 | 3/1979 |
| 2002/0108194 A1* | 8/2002 | Carlucci et al. | 15/28 | DE | 82 15 26637 U1 | 9/1982 |
| 2002/0116775 A1 | 8/2002 | Wong | 15/22.1 | DE | 3114507 | 3/1983 |
| 2002/0138926 A1* | 10/2002 | Brown et al. | 15/22.1 | DE | 3337054 | 10/1985 |
| 2002/0138928 A1* | 10/2002 | Calabrese | 15/22.1 | DE | 35 29 953 A1 | 3/1987 |
| 2002/0157198 A1* | 10/2002 | Biro et al. | 15/22.1 | DE | 3615936 | 11/1987 |
| 2002/0192621 A1 | 12/2002 | Ben-Ari | | DE | 27 15414 | 1/1988 |
| 2003/0033680 A1 | 2/2003 | Davies et al. | | DE | 37 44 630 A1 | 7/1989 |
| 2003/0033682 A1 | 2/2003 | Davies et al. | 15/110 | DE | 39 289 19 A1 | 3/1991 |
| 2003/0041402 A1 | 3/2003 | Stein | | DE | 4023870 | 1/1992 |
| 2003/0066147 A1 | 4/2003 | Roh | | DE | 42 07 968 | 9/1993 |
| 2003/0077107 A1 | 4/2003 | Kuo | 401/278 | DE | 94 00 231 | 3/1994 |
| 2003/0079304 A1 | 5/2003 | Dworzan | | DE | 44 12 301 | 10/1995 |
| 2003/0084525 A1 | 5/2003 | Blaustein | | DE | 198 17 704 | 4/1998 |
| 2003/0084528 A1 | 5/2003 | Chan | | DE | 29919053 | 12/2000 |
| 2003/0140440 A1 | 7/2003 | Gavney, Jr. | 15/117 | DE | 100 28 530 A1 | 12/2001 |
| 2003/0159224 A1 | 8/2003 | Fischer et al. | | DE | 20111428 U1 | 1/2003 |
| 2003/0196283 A1 | 10/2003 | Eliav et al. | 15/22.1 | DK | 0076598 | 11/1953 |
| 2003/0229959 A1 | 12/2003 | Gavney, Jr. et al. | 15/117 | EP | 0 189 816 A2 | 8/1986 |
| 2004/0010869 A1 | 1/2004 | Fattori et al. | 15/22.1 | EP | 0322562 | 5/1989 |
| 2004/0016067 A1 | 1/2004 | Kraemer | | EP | 0 360 766 | 3/1990 |
| 2004/0025275 A1 | 2/2004 | Moskovich et al. | 15/167.1 | EP | 0 520 985 B1 | 9/1991 |
| 2004/0060132 A1 | 4/2004 | Gatzemeyer et al. | 15/22.1 | EP | 0 704 179 A1 | 4/1996 |
| 2004/0060133 A1 | 4/2004 | Eliav | 15/22.1 | EP | 0 972 464 A1 | 1/2000 |
| 2004/0060134 A1 | 4/2004 | Eliav et al. | 15/22.1 | EP | 0857026 B1 * | 1/2000 |
| 2004/0060135 A1 | 4/2004 | Gatzemeyer et al. | 15/22.1 | EP | 0968686 | 5/2000 |
| 2004/0060136 A1 | 4/2004 | Gatzemeyer et al. | 15/22.1 | EP | 1004282 | 5/2000 |
| 2004/0060137 A1 | 4/2004 | Eliav | 15/22.1 | EP | 0 783 850 B1 | 3/2001 |
| 2004/0068809 A1 | 4/2004 | Weng | | EP | 1 080 664 | 3/2001 |
| 2004/0083566 A1 | 5/2004 | Blaustein et al. | | EP | 0 870 440 B1 | 12/2001 |
| 2004/0084063 A1 | 5/2004 | Vago | | EP | 1 320 309 A | 6/2003 |
| 2004/0123409 A1 | 7/2004 | Dickie | | EP | 1 661 487 | 5/2006 |
| 2004/0128784 A1 | 7/2004 | Ben-Ari | | EP | 1 700 537 A1 | 9/2006 |
| 2004/0154112 A1* | 8/2004 | Braun et al. | 15/22.1 | EP | 1 449 496 B1 | 9/2008 |
| 2004/0168271 A1 | 9/2004 | McDougall | 15/28 | FR | 459 442 | 11/1913 |
| 2004/0177458 A1 | 9/2004 | Chan | | FR | 829086 | 10/1938 |
| 2004/0177462 A1* | 9/2004 | Brown et al. | 15/167.1 | FR | 936529 | 12/1946 |
| 2004/0221409 A1 | 11/2004 | Gavney, Jr. | 15/117 | FR | 1075171 | 10/1954 |
| 2004/0231076 A1 | 11/2004 | Gavney, Jr. | 15/22.1 | FR | 1 300 138 | 4/1961 |
| 2004/0231082 A1 | 11/2004 | Gavney, Jr. | 15/110 | FR | 2541100 | 8/1984 |
| 2004/0237236 A1 | 12/2004 | Gavney, Jr. | 15/117 | FR | 2548528 | 1/1985 |
| 2004/0261203 A1 | 12/2004 | Dworzan | | FR | 2559361 | 8/1985 |
| 2005/0015901 A1 | 1/2005 | Gavney, Jr. | 15/28 | FR | 2 612 751 | 9/1988 |
| 2005/0060822 A1 | 3/2005 | Chenvainu et al. | | FR | 2 616 306 | 12/1988 |
| 2005/0235439 A1 | 10/2005 | Braun et al. | | FR | 2789887 | 8/1999 |
| 2005/0273961 A1 | 12/2005 | Moskovich et al. | | FR | 2 789 887 | 8/2000 |
| 2006/0272112 A9 | 12/2006 | Masterman et al. | | GB | 193 601 A | 3/1923 |
| 2007/0251040 A1 | 11/2007 | Braun et al. | | GB | 280 067 A | 11/1927 |
| 2008/0060155 A1 | 3/2008 | Braun et al. | | GB | 378 129 A | 8/1932 |
| 2008/0178401 A1 | 7/2008 | Claire et al. | | GB | 490 892 A | 8/1938 |
| 2009/0172900 A1 | 7/2009 | Brown, Jr. et al. | | GB | 690 422 A | 4/1953 |
| 2010/0162499 A1 | 7/2010 | Braun et al. | | GB | 1 164 597 A | 9/1969 |
| | | | | GB | 1 325 860 A | 8/1973 |
| | FOREIGN PATENT DOCUMENTS | | | GB | 1 537 526 | 12/1978 |
| BE | 894944 | 1/1983 | | GB | 2137080 | 10/1984 |
| CA | 454913 | 3/1949 | | GB | 2214420 | 6/1989 |
| CA | 1268011 | 3/1986 | | GB | 2 214 420 A | 9/1989 |
| CA | 2483825 | 10/2004 | | GB | 2247297 | 2/1992 |

| | | |
|---|---|---|
| GB | 2 354 432 A | 3/2001 |
| GB | 2371217 | 7/2002 |
| JP | 50-11769 | 2/1975 |
| JP | 51-056165 U | 5/1976 |
| JP | 52-125962 U | 9/1977 |
| JP | 55-122633 U | 9/1980 |
| JP | 58-091931 U | 6/1983 |
| JP | 59-066433 U | 5/1984 |
| JP | 61-090877 | 5/1986 |
| JP | 61-187531 U | 11/1986 |
| JP | 63-066928 U | 5/1988 |
| JP | 1-72128 | 3/1989 |
| JP | 2-119031 | 4/1990 |
| JP | 2-180203 | 7/1990 |
| JP | 3-3226 | 1/1991 |
| JP | 3-312978 | 9/1991 |
| JP | 4-123121 | 11/1992 |
| JP | 4-128627 | 11/1992 |
| JP | 5-69342 | 3/1993 |
| JP | 5-76416 | 3/1993 |
| JP | 05096597 | 4/1993 |
| JP | 5-123222 | 5/1993 |
| JP | 6-327517 A2 | 11/1994 |
| JP | 8103326 | 4/1996 |
| JP | 8103332 | 4/1996 |
| JP | 8257043 | 8/1996 |
| JP | 8299372 | 11/1996 |
| JP | 9-140456 | 3/1997 |
| JP | 9-187319 A2 | 7/1997 |
| JP | 10137038 | 5/1998 |
| JP | 1997-140456 | 12/1998 |
| JP | 2000-157338 | 6/2000 |
| JP | 2000-300345 | 10/2000 |
| JP | 2000-300347 | 10/2000 |
| JP | 2000-308524 | 11/2000 |
| JP | 2001-190333 | 7/2001 |
| JP | 2001-507360 | 7/2001 |
| JP | 2002-010832 | 1/2002 |
| JP | 2002-248118 | 9/2002 |
| JP | 2003-061986 | 3/2003 |
| JP | 2003-093415 | 4/2003 |
| JP | 2003-164473 | 6/2003 |
| RU | 2045216 | 10/1995 |
| RU | 2100001 C | 12/1997 |
| RU | 2161018 | 12/2000 |
| SU | 1752336 A1 | 5/1990 |
| SU | 1687243 | 10/1991 |
| WO | WO 91/05088 | 4/1991 |
| WO | WO 92/04589 | 3/1992 |
| WO | PCT/93/14671 | 8/1993 |
| WO | WO 93/24034 | 12/1993 |
| WO | WO 94/03125 | 2/1994 |
| WO | WO 95/01113 A1 | 1/1995 |
| WO | WO 96/15696 | 5/1996 |
| WO | WO 96/20654 | 7/1996 |
| WO | WO 96/23431 | 8/1996 |
| WO | WO 96/28994 | 9/1996 |
| WO | WO 97/14330 | 4/1997 |
| WO | WO 98/01055 | 1/1998 |
| WO | WO 98/18364 | 5/1998 |
| WO | WO 99/37181 | 7/1999 |
| WO | WO 00/21406 | 4/2000 |
| WO | WO 00/30495 | 6/2000 |
| WO | WO 00/34022 | 6/2000 |
| WO | WO 00/47083 | 8/2000 |
| WO | WO 00/64307 | 11/2000 |
| WO | WO 00/76369 A2 | 12/2000 |
| WO | WO 01/01817 | 1/2001 |
| WO | WO 01/06947 A1 | 1/2001 |
| WO | WO 01/06946 A1 | 2/2001 |
| WO | WO 01/21036 | 3/2001 |
| WO | WO 01/43586 | 6/2001 |
| WO | WO 01/89344 | 11/2001 |
| WO | WO 02/05679 A1 | 1/2002 |
| WO | WO 02/11583 A2 | 2/2002 |
| WO | WO 02/19942 | 3/2002 |
| WO | 02/38004 | 5/2002 |
| WO | WO 02/45617 | 6/2002 |
| WO | WO 02455617 | 6/2002 |
| WO | WO 03/015575 A1 | 2/2003 |
| WO | WO 03/055351 A1 | 7/2003 |
| WO | WO 03/086140 A1 | 10/2003 |
| WO | WO 2004/014181 A1 | 2/2004 |
| WO | WO 2004/028235 A2 | 4/2004 |
| WO | WO 2004/062519 A2 | 7/2004 |
| WO | WO 2004/062573 A2 | 7/2004 |
| WO | WO 2004/071237 A1 | 8/2004 |

OTHER PUBLICATIONS

Interplak Opticlean Replacement Brush Heads, Model RBG3.
International Designs Bulletin, Aug. 1998, DM/045 025 Trisa Holding AG "Toothbrush Heads".
Office Action from a foreign patent office in a counterpart application (European Application No. 04 705 730.2) dated May 2, 2007.
Photograph of Interplak EZbrush electric toothbrush, believed to have been available on or before Sep. 19, 2003, 1 page.
U.S. Appl. No. 12/186,639, Aug. 6, 2008, Braun et al.
Board Opinion from the Chinese Patent Office with regard to Application No. 01806615.1 dated Jul. 17, 2007 with translation.
Office Action for U.S. Appl. No. 10/389,448 dated Feb. 25, 2009; Braun et al.; filed Mar. 14, 2003.
Office Action for U.S. Appl. No. 10/389,448 dated Jun. 2, 2006; Braun et al.; filed Mar. 14, 2003 (3801cc).
Office Action for U.S. Appl. No. 10/389,448 dated Oct. 26, 2007; Braun et al.; filed Mar. 14, 2003.
Office Action for U.S. Appl. No. 10/389,448 dated Jul. 2, 2008; Braun et al.; filed Mar. 14, 2003.
Office Action for U.S. Appl. No. 10/389,448 dated Apr. 4, 2008; Braun et al.; filed Mar. 14, 2003.
Office Action for U.S. Appl. No. 10/389,448 dated Feb. 22, 2007; Braun et al.; filed Mar. 14, 2003.
Office Action for U.S. Appl. No. 11/825,387 dated Feb. 19, 2010; Braun et al.; filed Jun. 22, 2010.
Office Action for U.S. Appl. No. 11/825,387 dated Feb. 19, 2010; Braun et al.; filed Jul. 6, 2007.
Office Action for U.S. Appl. No. 11/825,387 dated Feb. 11, 2009; Braun et al.; filed Jul. 6, 2007.
Office Action for U.S. Appl. No. 11/825,387 dated Aug. 29, 2008; Braun et al.; filed Jul. 6, 2007.
Office Action for U.S. Appl. No. 11/825,387 dated Dec. 6, 2007; Braun et al.; filed Jul. 6, 2007.
Office Action for U.S. Appl. No. 12/186,639 dated Jun. 22, 2010; Braun et al.; filed Aug. 6, 2008.
Office Action for U.S. Appl. No. 12/186,639 dated Dec. 23, 2009; Braun et al.; filed Aug. 6, 2008.
Office Action for U.S. Appl. No. 12/186,639 dated Aug. 6, 2008; Braun et al.; filed Aug. 6, 2008.
Office Action for U.S. Appl. No. 12/186,639 dated Sep. 2, 2010; Braun et al.; filed Aug. 6, 2008.
Office Action for U.S. Appl. No. 10/830,693 dated Feb. 26, 2009; Masterman et al.; filed Apr. 23, 2004.
Distinctive Plastics—Multi-Component Molding" http://www.distinctiveplastics.com/html/?id=2 copyright 2006.
Office Action for U.S. Appl. No. 10/830,693 dated Jul. 2, 2008; Masterman et al.; filed Apr. 23, 2004.
Office Action for U.S. Appl. No. 10/830,693 dated Mar. 3, 2008; Masterman et al.; filing date Apr. 23, 2004.
Office Action for U.S Appl. No. 10/830,693 dated Oct. 24, 2007; Masterman et al; filing date Apr. 23, 2004.
Office Action for U.S. Appl. No. 10/830,693 dated May 15, 2007; Masterman et al.; filing date Apr. 23, 2004.
Office Action for U.S. Appl. No. 10/830, 693 dated Aug. 17, 2006; Masterman et al.; filing date Apr. 23, 2004.
Office Action for U.S. Appl. No. 10/799,793 dated Jun. 19, 2009; Braun et al.; filing date May 2, 2007.
Office Action for U.S. Appl. No. 10/799,793 dated Apr. 25, 2008; Braun et al.; filing date May 2, 2007.
Office Action for U.S. Appl. No. 10/799,793 dated Mar. 12, 2004; Braun et al.; filing date May 2, 2007.
Office Action for U.S. Appl. No. 10/799,793 dated Apr. 18, 2007; Braun et al.; filing date May 2, 2007.

Office Action for U.S. Appl. No. 10/799,793 dated Dec. 27, 2007; Braun et al.; filing date May 2, 2007.
Office Action for U.S. Appl. No. 10/820,562 dated Jun. 22, 2010; Braun et al.; filing date Mar. 16, 2000.
Office Action for U.S. Appl. No. 10/820,562 dated Dec. 2, 2008; Braun et al.; filing date Mar. 16, 2000.
Office Action for U.S. Appl. No. 10/820,562 dated Jul. 27, 2009; Braun et al.; filing date Mar. 16, 2000.
Office Action for U.S. Appl. No. 10/820,562 dated Jul. 5, 2007; Braun et al.; filing date Mar. 16, 2000.
Office Action for U.S. Appl. No. 10/820,562 dated May 8, 2006; Braun et al.; filing date Mar. 16, 2000.
Office Action for U.S. Appl. No. 10/820,562 dated Aug. 15, 2005; Braun et al.; filing date Mar. 16, 2000.
Office Action for U.S. Appl. No. 10/389,448 dated Jun. 2, 2006; Braun et al.; filing date Mar. 14, 2003.
Office Action for U.S. Appl. No. 10/389,448 dated Oct. 26, 2007; Braun et al.; filing date Mar. 14, 2003.
Office Action for U.S. Appl. No. 10/389,448 dated Jul. 2, 2008; Braun et al.; filing date Mar. 14, 2003.
Office Action for U.S. Appl. No. 09/421,747 dated Jul. 16, 2001; Devlin et al., filing date Oct. 20, 1999.
Office Action for U.S. Appl. No. 09/421,747 dated Nov. 9, 2001; Devlin et al., filing date Oct. 20, 1999.
Office Action for U.S. Appl. No. 09/421,747 dated Jan. 7, 2002; Devlin et al., filing date Oct. 20, 1999.
Office Action for U.S. Appl. No. 09/573,576 from Jan. 29, 2003 to Sep. 17, 2004 from Chenvainu et al.
Office Action for U.S. Appl. No. 09/634,087 from Jun. 24, 2003 to Aug. 17, 2005 from Braun et al.
European Search Report for.
International Search Report for.
Office Action for U.S. Appl. No. 08/887,866 dated Oct. 13, 1999; Roberts, filing date Jul. 3, 1997.
Office Action for U.S. Appl. No. 08/887,866 dated Mar. 26, 1999; Roberts, filing date Jul. 3, 1997.
Office Action for U.S. Appl. No. 08/887,866 dated Sep. 17, 1999; Roberts, filing date Jul. 3, 1997.

* cited by examiner

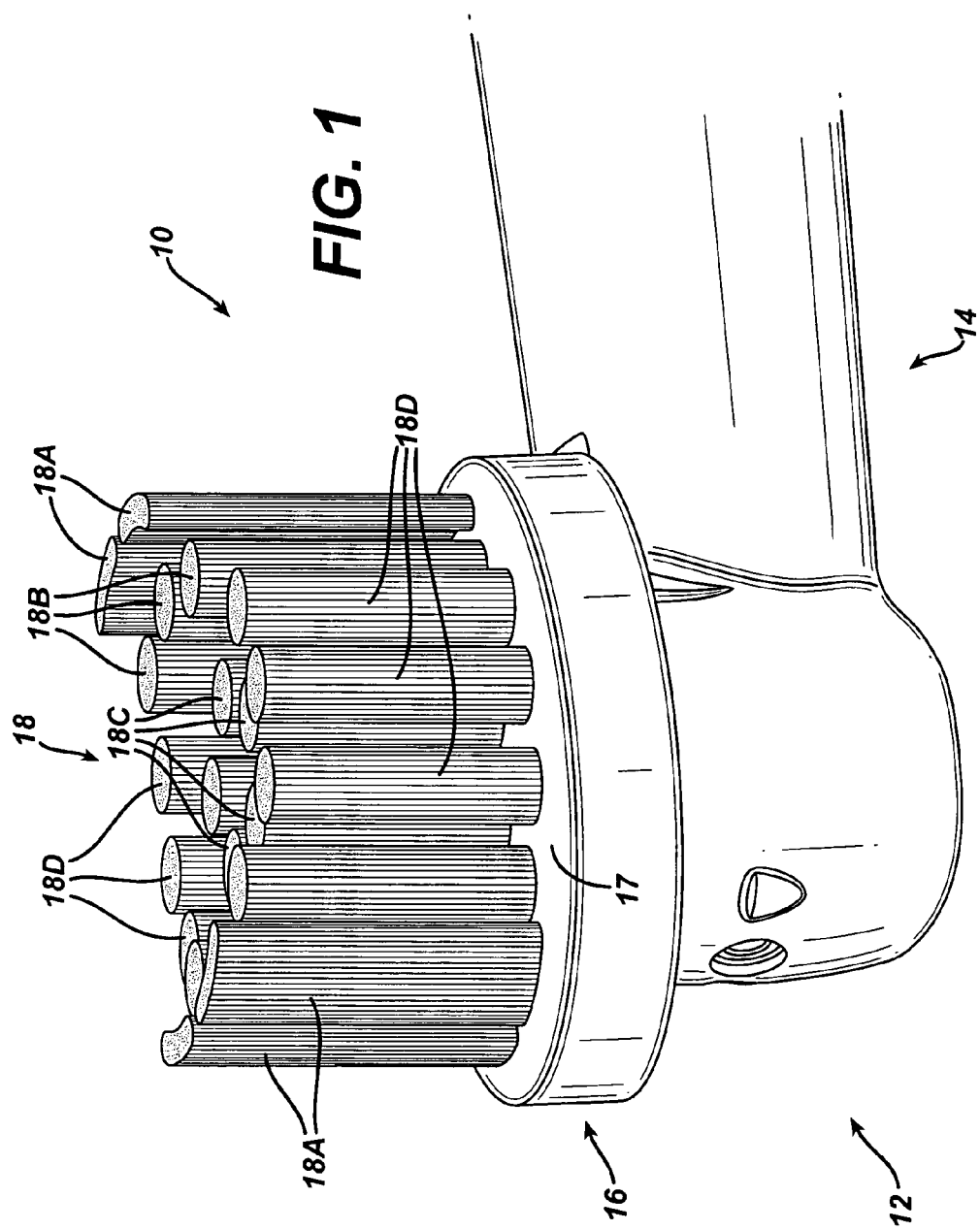

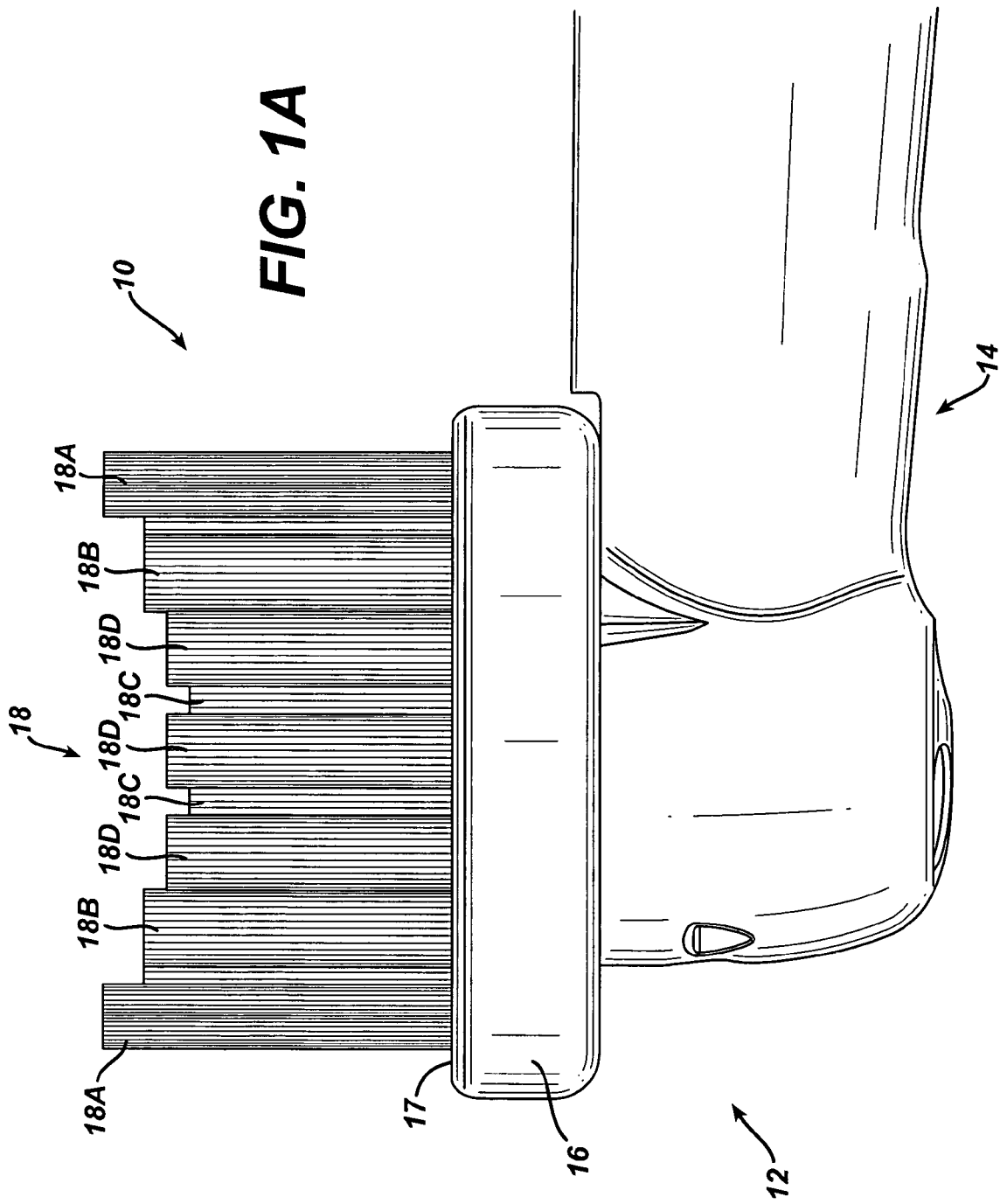

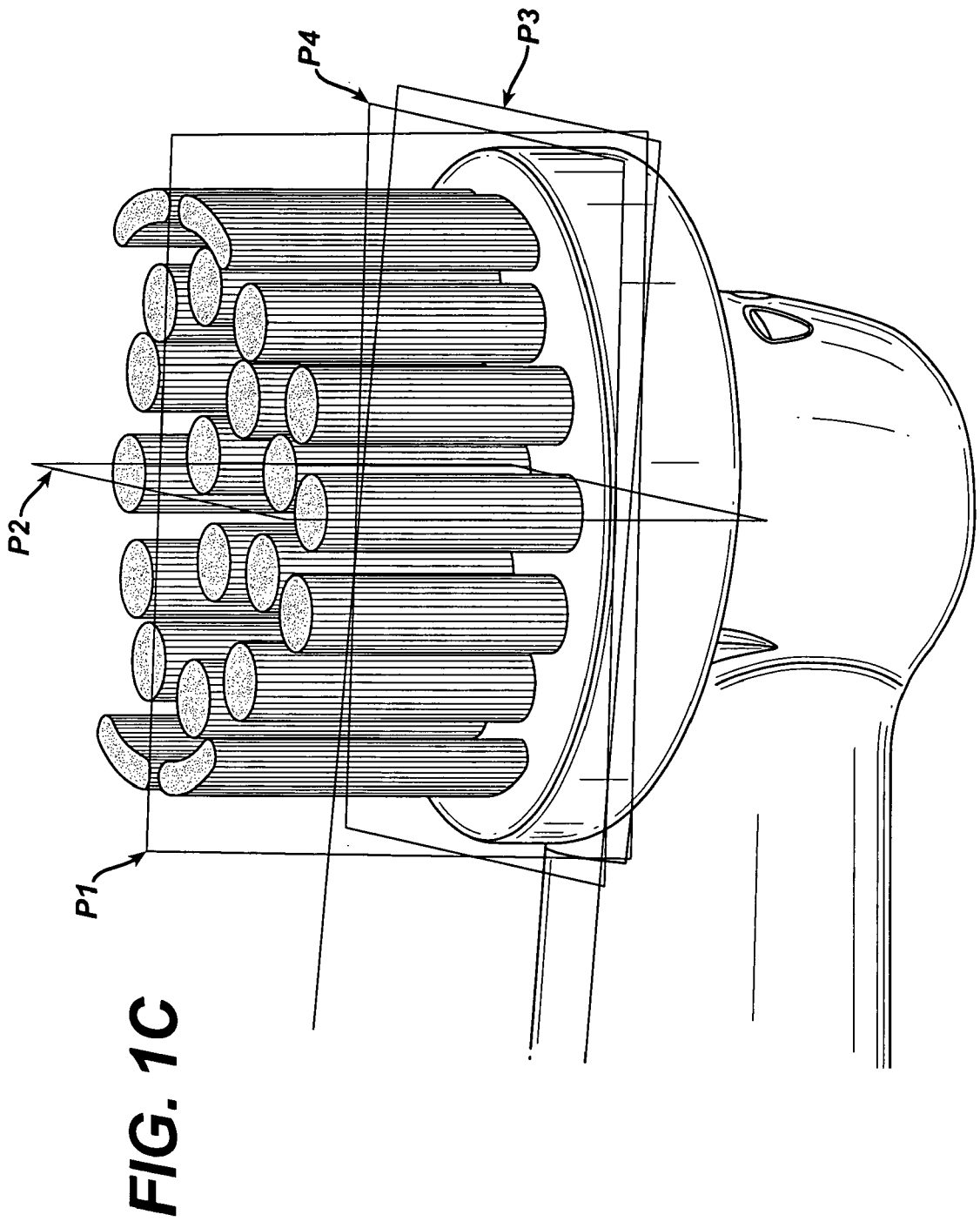

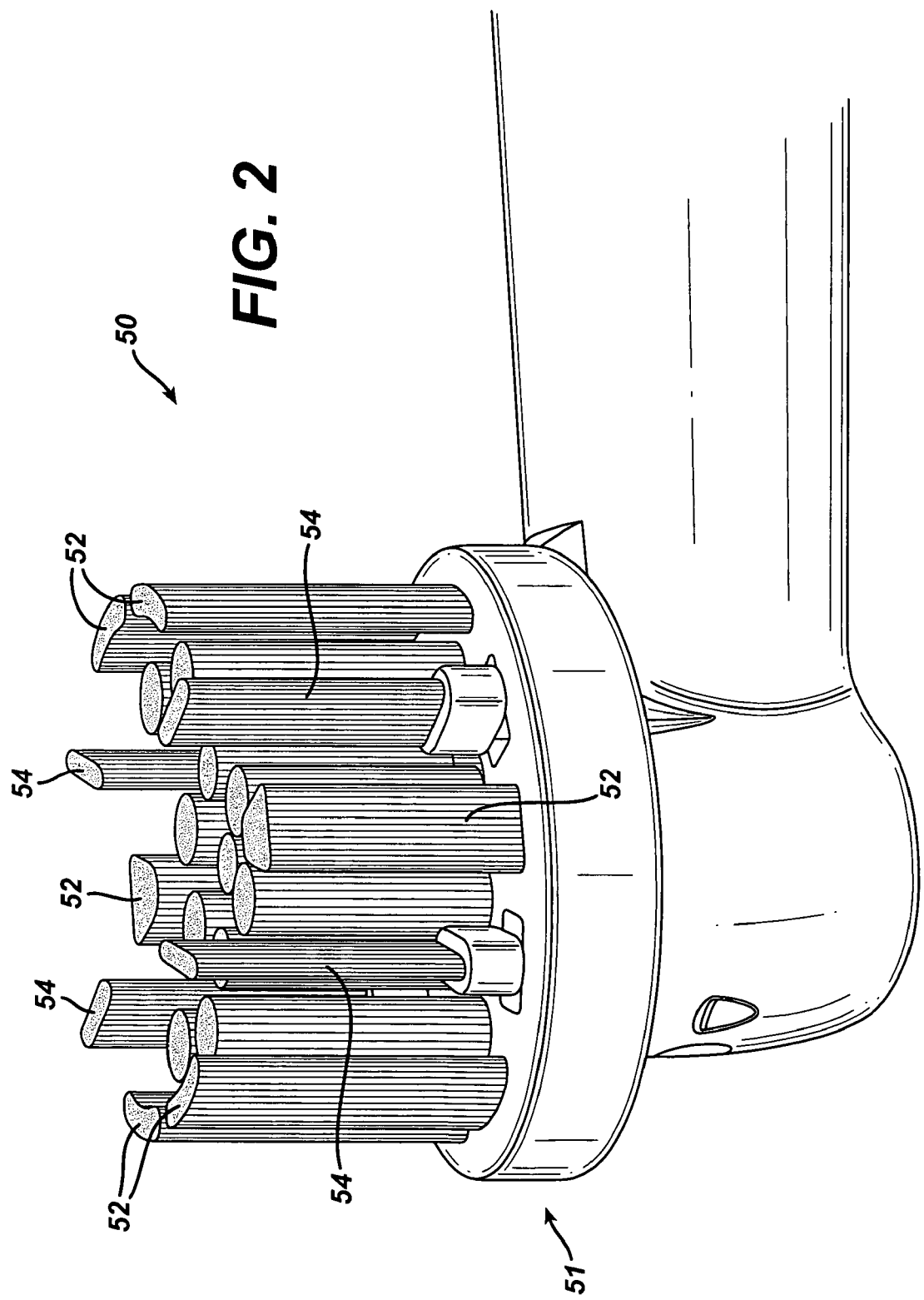

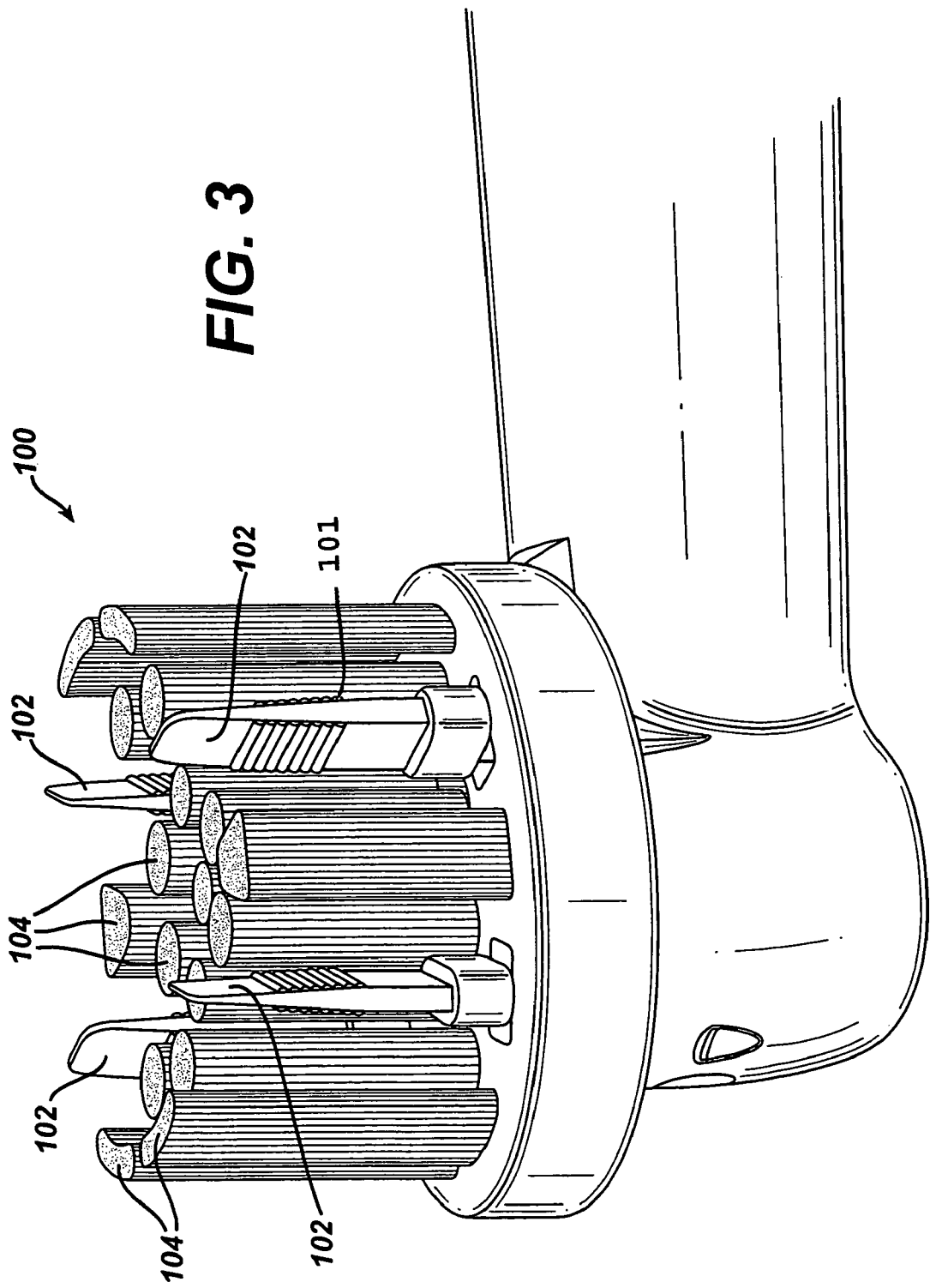

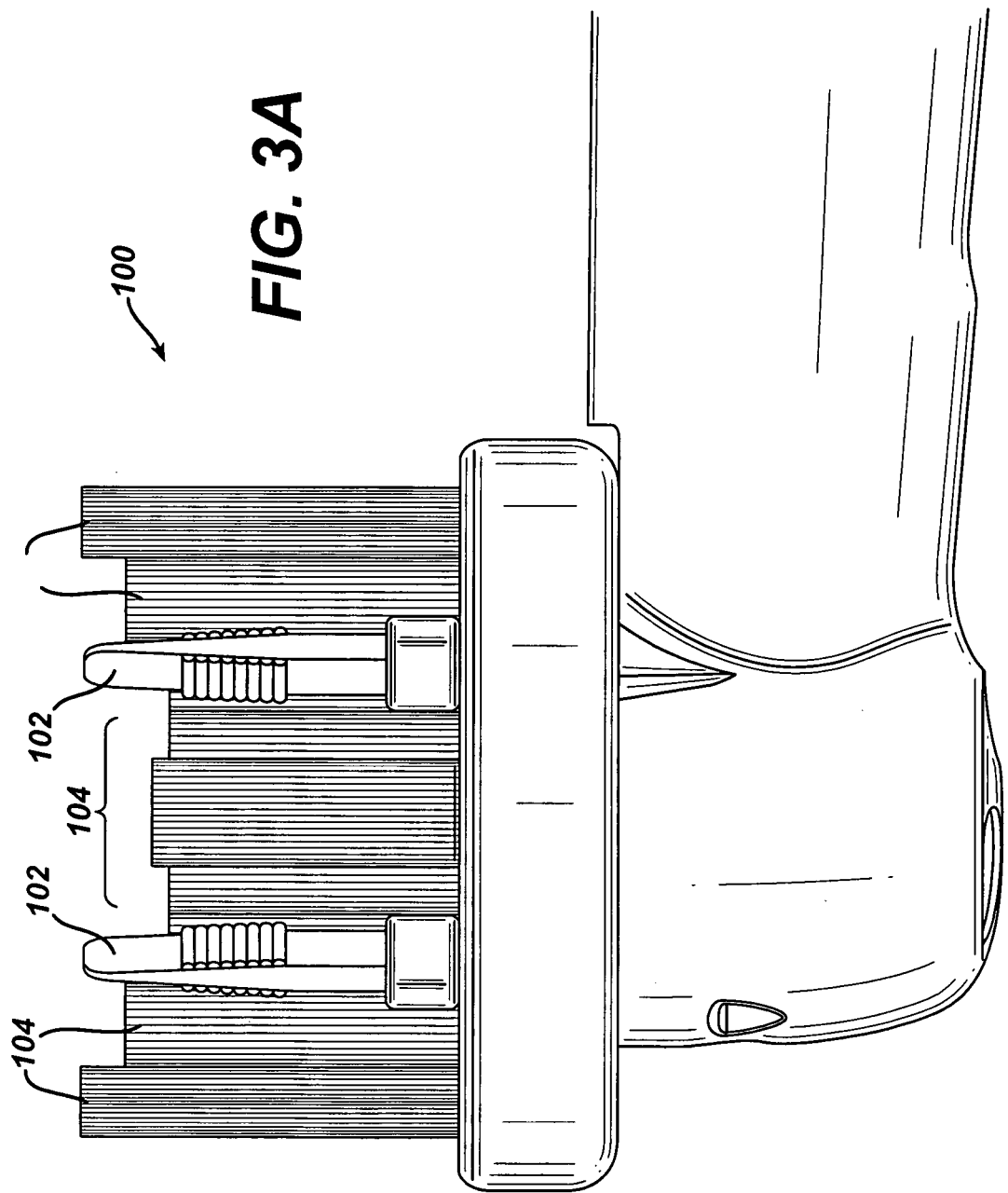

TOOTHBRUSHES

TECHNICAL FIELD

This invention relates to toothbrushes, and more particularly to power toothbrushes.

BACKGROUND

Power toothbrushes are well known and have been on the market for years. In typical power toothbrushes, tufts of bristles on the brush head extend generally perpendicularly from the top surface of the head. The head is oscillated, rotated and/or translated in order to provide enhanced tooth cleaning capability.

In many power toothbrushes, the top surface of the head is generally circular in shape, and is dimensioned to clean the larger teeth one at a time and smaller teeth two at a time, with most of the bristles typically contacting the tooth or teeth during brushing. In some power toothbrushes, the head has a generally oval shape.

SUMMARY

In general, the invention features power toothbrush heads having particular arrangements of bristles and/or tufts of bristles, power toothbrushes including such heads, and methods of using such heads and toothbrushes.

In one aspect, the invention features a head for a power toothbrush including an elongated support member, and a plurality of bristles extending from the support member, at least some of the bristles having different heights, the bristles being arranged so that their heights are symmetric, in a non-translatable mirror image symmetry, about two planes of symmetry.

In another aspect, the invention features a head for a power toothbrush including an elongated support member, and a plurality of tufts of bristles extending from the support member, the tufts of bristles having at least three different heights, the tufts being arranged so that their tips define a rounded contour.

Some implementations of these aspects include one or more of the following features. The bristles or tufts have may different lengths, measured from a top surface of the support member. Alternatively, or in addition, the bristles or tufts may extend the same length from a top surface of the support member, and the top surface is contoured so that the bristles or tufts have different heights as measured from a horizontal plane taken through the lowest point on the top surface. The two planes of symmetry may be arranged about a central axis of the brush head. The bristles may be arranged in an array and tips of the bristles define a continuously curved surface. The two planes of symmetry may intersect in the vicinity of the center of the elliptical support member. The head may be configured for use on a power toothbrush having a rotationally oscillating motion. The tufts of bristles may have at least four different heights. The rounded contour may be lowest adjacent a pivot point of the head. A top surface of the support member may have an overall surface area of from about 170 to 200 mm². The head may further include one or more elastomeric element(s). The tufts may be arranged so that their heights are symmetric about two planes of symmetry. The height of the tallest bristles may be from about 20 to 50% greater than the height of the shortest bristles. A top surface of the support member may have a length of about 14 to 19 mm, e.g., about 16 to 17 mm. The top surface may have a width of about 12 to 15 mm, e.g., about 13 to 14 mm. The top surface may have an aspect ratio (length/width) of about 1.2 to 1. The top surface may have a shape selected from the group consisting of oval, ellipse, rounded diamond, and rounded rectangle. The top surface may have a concave shape.

In a further aspect, the invention features a power toothbrush including a handle, and, extending from the handle, a head including an elongated support member, and a plurality of bristles extending from the support member, at least some of the bristles having different heights, the bristles being arranged so that their heights are symmetric, in a non-translatable mirror image symmetry, about two planes of symmetry.

In yet another aspect, the invention features a power toothbrush including a handle, and, extending from the handle, a head including an elongated support member, and a plurality of tufts of bristles extending from the support member, the tufts of bristles having at least three different heights, the tufts being arranged so that their tips define a rounded contour.

Some implementations of these aspects may include one or more of the features discussed above.

The invention also features, in another aspect, a head for a power toothbrush including an elongated support member, and a plurality of bristles extending from the support member, at least some of the bristles having different heights, the heights of the bristles being selected to provide a bristle tip contour that allows substantially all of the bristle tips to contact the dentition simultaneously during brushing.

In another aspect, the invention features methods of brushing teeth including contacting the teeth with bristles of one of the power toothbrushes discussed above.

In some implementations, the contour of the bristles or bristle tufts allows all or substantially all of the bristle tips to contact the dentition (tooth surface) when the toothbrush head is brushing one or more teeth of a user. Whether this occurs in a given implementation may be determined, e.g., by high speed videography. In some cases, the support surface from which the bristles extend is generally elongated, and the contour allows all of the bristle tips, including those at the distal ends of the head, to contact the dentition. As a result, a longer surface may be cleaned simultaneously, as compared to a flat brush having the same area or shape as projected onto a flat plane. Such brush heads also generally feel comfortable in the mouth, and do not seem overly bulky. A toothbrush that is contoured to match the general curvature of the dentition also holds the support surface at a more consistent position (i.e. height and angle) above the teeth. This allows taller cleaning elements to be incorporated into the toothbrush that are spaced appropriately to reach in between the teeth and other areas that are normally difficult to access.

The details of one or more embodiments of the invention are set forth in the accompanying drawings and the description below. Other features and advantages of the invention will be apparent from the description and drawings, and from the claims.

DESCRIPTION OF DRAWINGS

FIG. 1 is a perspective view of a brush head according to one embodiment of the invention.

FIG. 1A is a side view of the brush head of FIG. 1.

FIG. 1C is a perspective view of a brush head similar to that shown in FIG. 1, except that the head is slightly tilted towards the handle, with planes of symmetry indicated.

FIG. 2 is a perspective view of a brush head according to an alternative embodiment.

FIG. 3 is a perspective view of a brush head according to another alternative embodiment.

FIG. 3A is a side view of the brush head of FIG. 3.

DETAILED DESCRIPTION

Figure 1B:
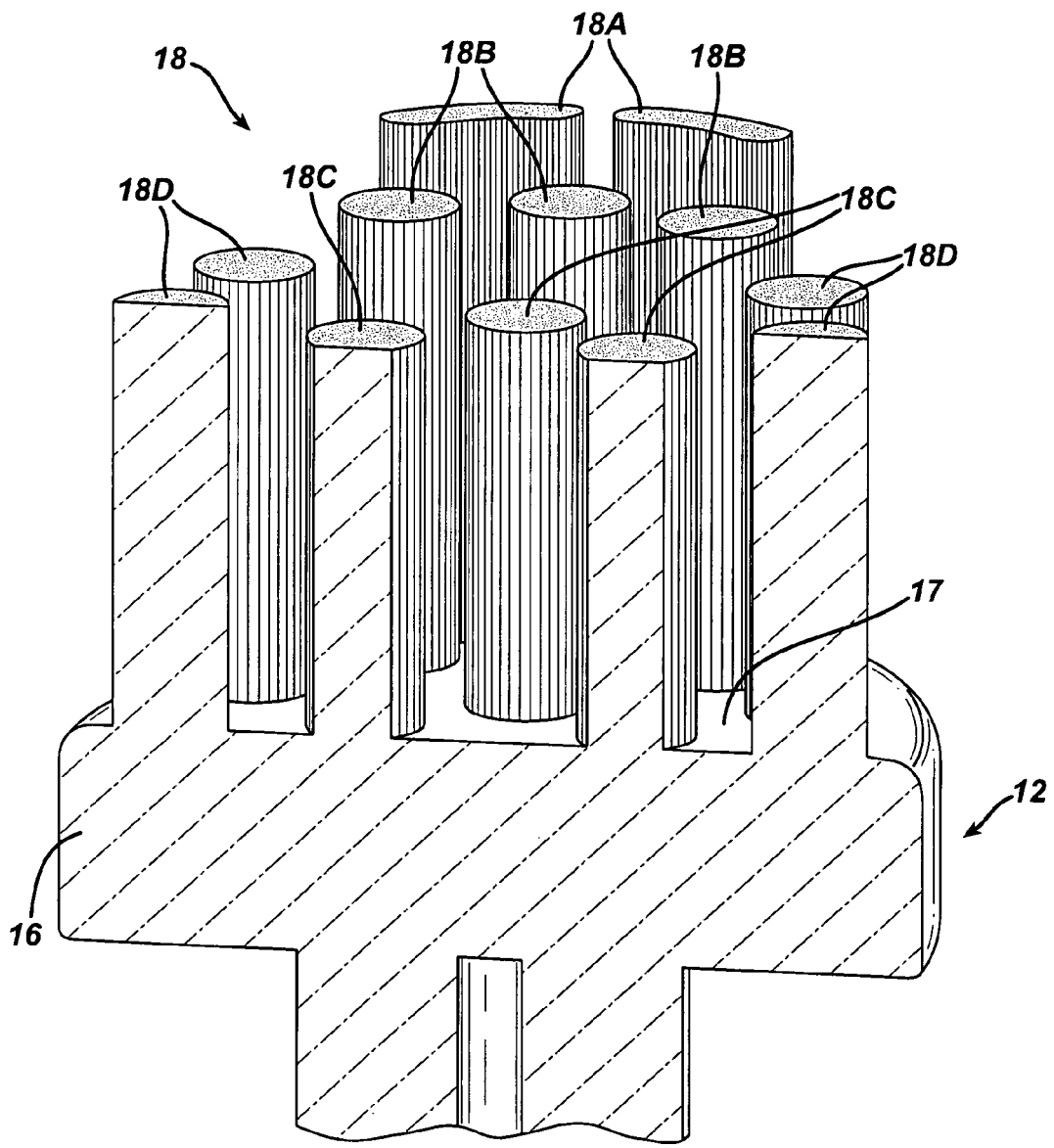
FIG. 1B is a transverse cut-away view of the brush head of FIG. 1.

Referring to FIG. 1, a power toothbrush 10 includes a head 12 and a neck 14. As is well known to those skilled in the art, head 12 is oscillated during brushing. Generally, the head 12 is oscillated in a rotating manner about an axis of rotation which typically extends through the center of the head but may be offset, as will be discussed below. An electric motor (not shown) oscillates the head through gearing, linkages, cranks, and/or other drive mechanisms as is well known. Electrical power may be supplied to the motor by rechargeable or primary (disposable) batteries. Further details as to how the head is oscillated will not be provided, as this aspect of the brush is not the focus of the invention.

Head 12 includes a generally elliptical support member 16 that is disposed approximately perpendicular to the axis of rotation of the head, and, extending from a top surface 17 of the support member 16, a plurality of bristle tufts 18. As will be discussed below, the top surface 17 typically is perpendicular to the axis of rotation, but may in some cases be tilted so that it is not perpendicular to the axis of rotation.

Although each tuft 18 is shown as a solid mass in the drawings, the tufts may each be made up of a great number of individual plastic bristles. The bristles may be made of any desired polymer, e.g., nylon 6.12 or 6.10, and may have any desired diameter, e.g., 4 to 8 mil. The tufts are supported at their bases by the support member, and may be held in place by any desired tufting technique as is well known in the art, e.g., by insert molding or a stapling process. The tufts may also be mounted to move on the support member, e.g., with a pivoting motion as will be discussed below with reference to FIGS. 2 and 3-3B.

The support member is generally elliptical, i.e., it has a long axis and a short axis. Preferably, the long axis has a length of about 14 to 19 mm, and the short axis has a length of about 12 to 15 mm. The ellipse may have an aspect ratio (long axis/short axis) of about 1.2 to 1. The head size is most preferably around 16 to 17 mm long by 13 to 14 mm wide. The overall surface area of the surface 17 of the support member is preferably about 170 to 200 mm$^2$ (0.270 to 0.305 sq in).

There is a height differential between the different bristle tufts. The curved, elongated interdental tufts 18A, i.e., the two tufts that are at each furthest edge of the support member, adjacent the long axis of the toothbrush neck 14 when the head 12 is at rest, are tallest. The round end tufts 18B that are immediately inboard of the interdental tufts 18A (three on each side) are the next tallest, followed by the side tufts 18D (three on each side), which are mounted along the edge of the support member between the two sets of round end tufts 18B. The shortest tufts are the inner tufts 18C, which are arranged in a ring of five tufts, inboard of the side and end tufts. The interdental tufts 18A may be, for example, about 20 to 50% taller than the inner tufts 18C, e.g., from about 7 to 8.5 mm in height, the end tufts 18B may be about 10 to 40% taller than the inner tufts 18C, e.g., about 6 to 8 mm in height, and the side tufts 18D may be, for example, about 0 to 25% taller than the inner tufts 18C, e.g., from about 5 to 7 mm in height.

Figure 1D:
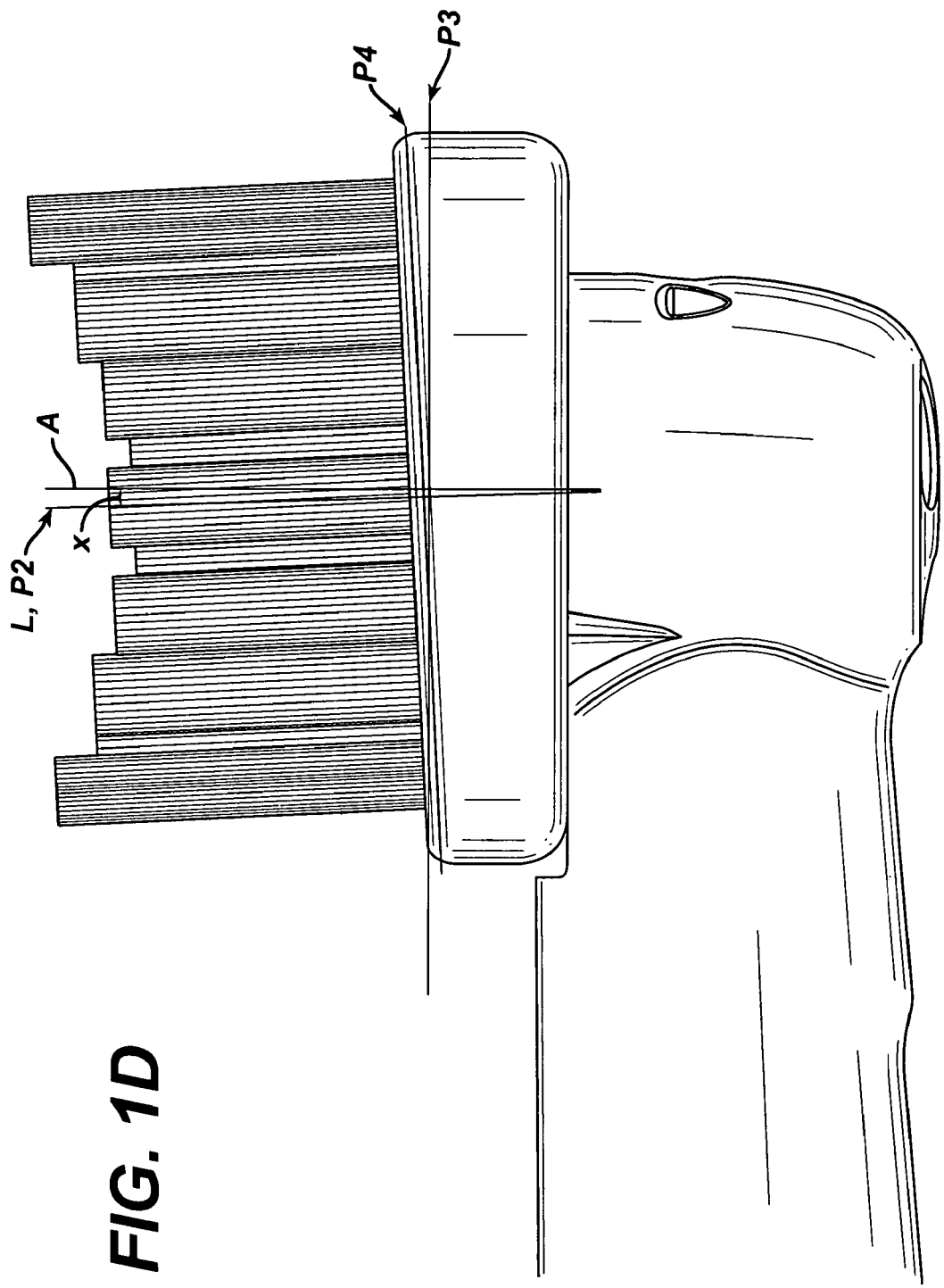
FIG. 1D is a side view of the brush head of FIG. 1C, with planes of symmetry indicated.

The contour produced by this height differential between the bristle tufts allows the tips of the bristles to conform closely to the shape of the dentition, allowing most or all of the bristles to contact the dentition during brushing of multiple teeth simultaneously. As shown in FIG. 1C, this contour is symmetric about two planes of symmetry, e.g., a plane (P1) taken through the long axis of the elliptical support member and a plane (P2) taken through the short axis of the support member. Both planes are perpendicular to the top surface 17 of the support member. It is noted that the line (L) defined by the intersection of these two planes (shown in FIG. 1D) may or may not be collinear with the axis of rotation (A) of the brush head. In the embodiment shown in FIGS. 1C and 1D, the axis of rotation A is perpendicular to a plane (P3) which is not parallel to or coplanar with the plane (P4) of the top surface 17 of the support member. The angle (X) between L and A is the result of the slight tilt of the brush head towards the handle, shown best in FIG. 1D. In other embodiments (e.g., the embodiment shown in FIGS. 1-1B), the axis of rotation A is perpendicular to plane P4.

The symmetry of the contour about planes P1 and P2 is a non-translatable mirror image symmetry, i.e., each quadrant is the mirror image of the two adjacent quadrants, but could not be "swapped" with either adjacent quadrant, i.e., "translated," without altering the contour defined by the tufts. Each quadrant can be rotated 180 degrees about the axis of symmetry defined by the intersection of planes P1 and P2 without altering the symmetry of the head, and each quadrant is a mirror image reflection of the adjacent quadrants. No quadrant can be translated without rotation, without altering the symmetry of the head.

As shown in FIG. 1B, in the embodiment shown in FIGS. 1-1B the top surface 17 of support member 16 is generally planar. As a result, the height differential is created by providing tufts of different lengths.

Figure 3B:
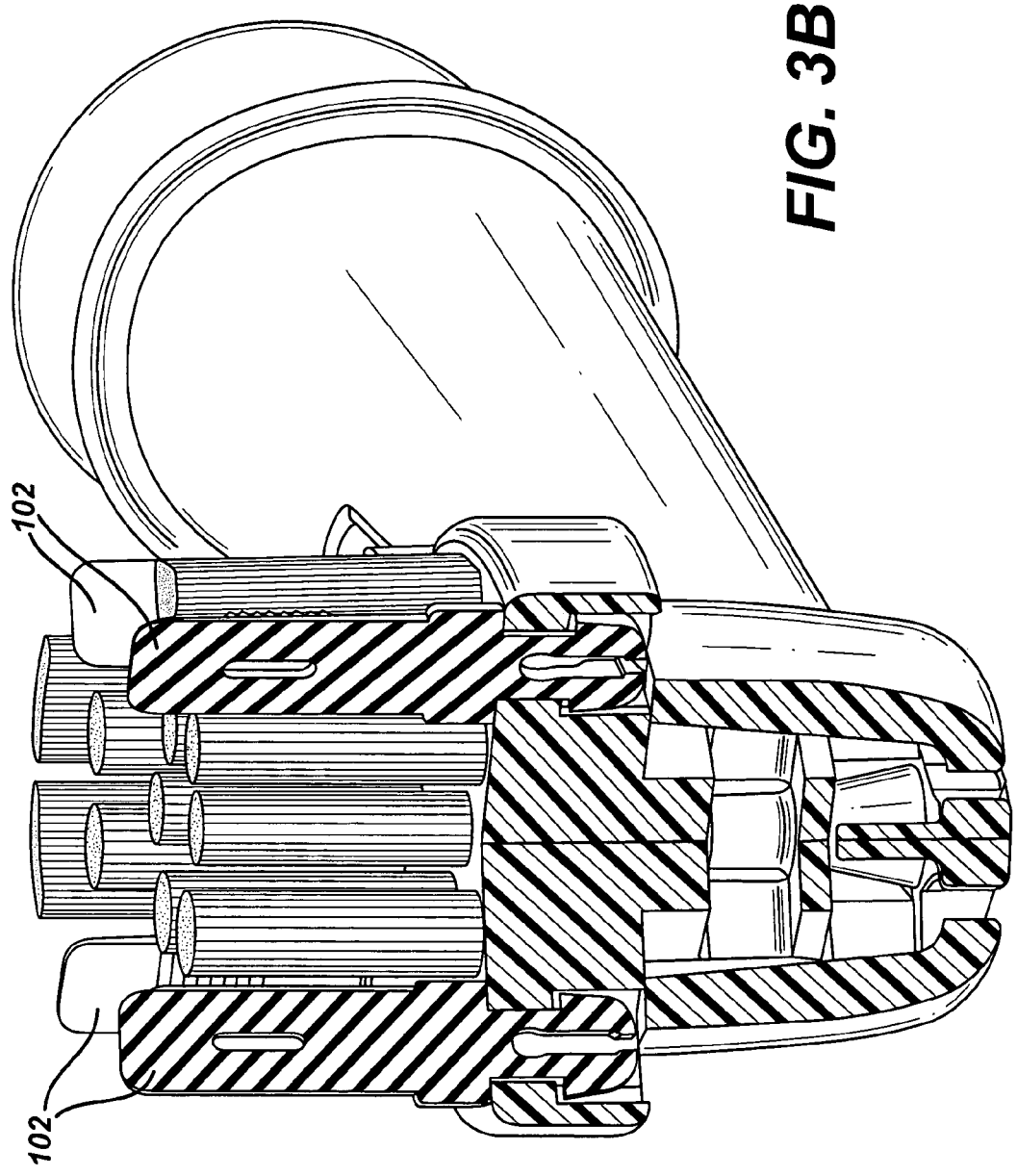
FIG. 3B shows the brush of FIG. 3 with a portion of the brush head cut away to show the pivoting mechanism.

The brush head may include pivoting tufts. For example, brush 50, shown in FIG. 2, includes a head 51 that carries a plurality of fixed tufts 52 and a plurality of pivoting tufts 54. The tufts are arranged to define a contour similar to that described above. Techniques for providing pivoting tufts are described in U.S. Pat. No. 6,553,604, the disclosure of which is incorporated by reference herein. One type of pivoting mechanism is shown in FIG. 3B in the context of pivoting elastomeric elements.

The brush head may also include elastomeric elements, in addition to or instead of tufts of bristles. For example, as shown in FIGS. 3 and 3A a toothbrush 100 includes elastomeric fins 102 and tufts of bristles 104, arranged to define a contour as discussed above. The elastomeric elements are sized for interproximal insertion, to provide cleaning and massage of the interproximal areas, as described in U.S. Ser. No. 10/389,448, filed Mar. 14, 2003. In the embodiment shown in FIGS. 3-3B the elastomeric fins are pivotably mounted, with each elastomeric fin optionally having a textured surface including ribs 101. However, the elastomeric elements may be stationary if desired, and the bristle tufts may be stationary or pivoting.

A number of embodiments of the invention have been described. Nevertheless, it will be understood that various modifications may be made without departing from the spirit and scope of the invention.

For example, while an elliptical support member has been shown and described above, the bristle contour described may be used with support members having other elongated shapes, e.g., oval, rounded diamond, or rounded rectangular.

Figure 4:
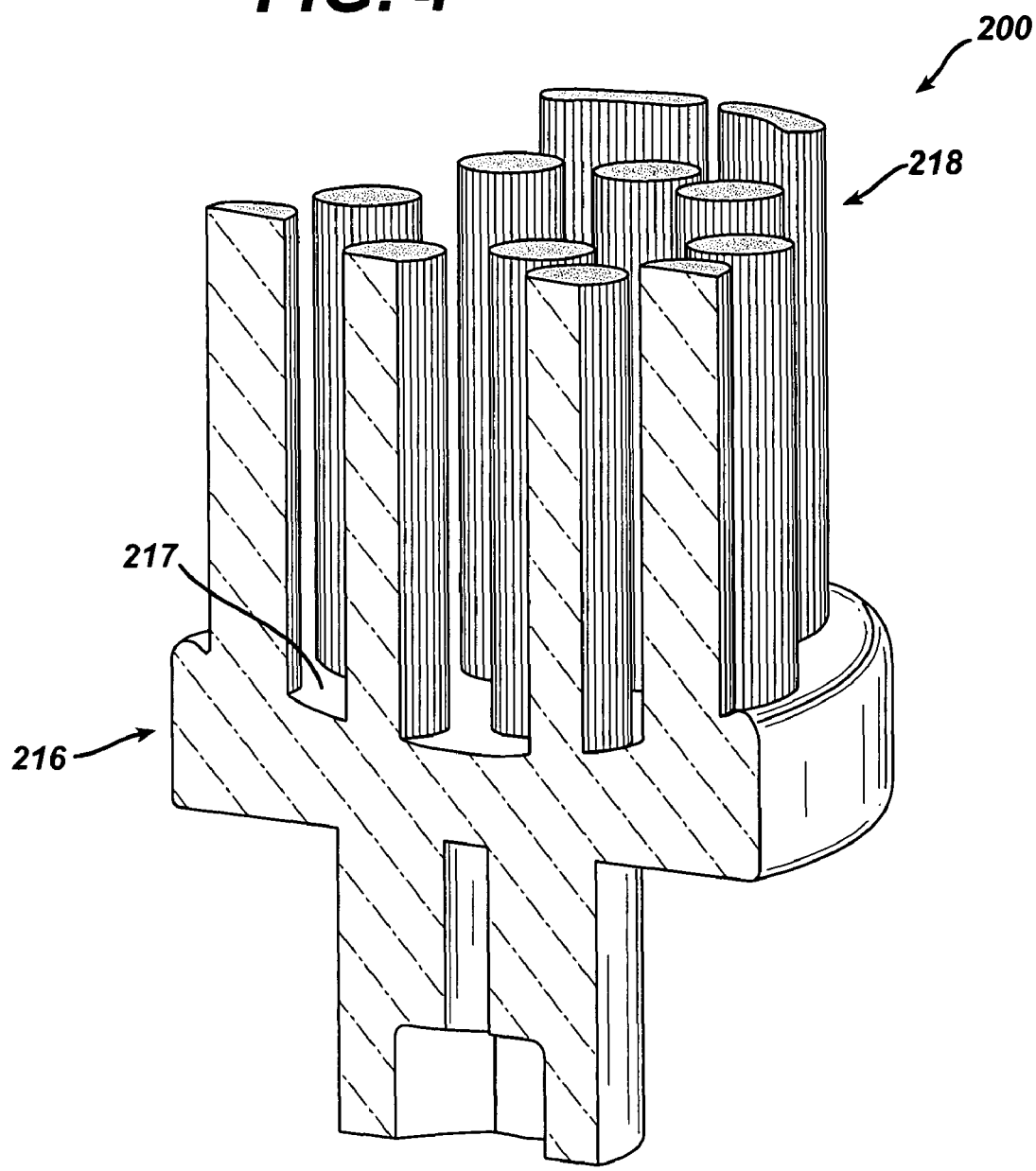
FIG. 4 is a transverse cut-away view of a brush head according to another alternative embodiment.

While, in the embodiments discussed above, the bristle height differential was determined by bristle length, in other embodiments the bristle height differential may be determined based on the geometry of the top surface of the support member. For example, as shown in FIG. 4, a brush head 200 includes a support member 216 having a concave top surface 217. In this embodiment, bristle tufts 218 are all of substantially the same length, but their heights define a contour similar to that described above due to the concave shape of the surface 217.

Moreover, while a brush head having four bristle heights is described above, other numbers of bristle heights may be used. For example, the bristle tufts may have three different heights, or five or more.

Alternatively, the bristles may be arranged in a uniform array, rather than tufts, and the height differential of their tips may define a continuously curved surface, e.g., a cup-shaped surface.

Additionally, while the contour shown in FIGS. 1-1A is symmetrical about two planes that intersect in the center of the surface 17 of the support member, symmetry could be defined about a point that is not centered on the support member.

While toothbrush heads having a plurality of elastomeric elements are shown in the figures and described above, some toothbrush heads may include a single elastomeric element. For example, the toothbrush head may include one of the elastomeric elements described in U.S. Ser. No. 10/364,148, filed Feb. 11, 2003, the disclosure of which is incorporated herein by reference.

Accordingly, other embodiments are within the scope of the following claims.

What is claimed is:

1. A power toothbrush comprising:
a handle,
a neck extending from the handle,
a motor within the handle, and
extending from the neck, a head including a support member, the support member including a lower portion constructed to be rotationally oscillated, relative to the neck, by the motor, and a top surface having an elongated shape selected from the group consisting of oval, elliptical and rounded diamond, a major axis of the elongated shape being disposed generally parallel to a long axis of the handle, wherein the top surface of the support member has an overall surface area of from about 170 to 200 mm$^2$,
a plurality of tufts of bristles extending from the support member, and
a plurality of elastomeric fins pivotably mounted in and extending from the support member, each elastomeric fin having a textured surface.

2. The power toothbrush of claim 1 wherein the textured surface comprises ribs.

3. The power toothbrush of claim 1 wherein the tufts of bristles and elastomeric fins, in combination, have at least three different heights.

4. The power toothbrush of claim 1 wherein the tufts of bristles and elastomeric fins, in combination, and arranged so that their tips define a rounded contour.

5. The power toothbrush of claim 1 wherein the major axis of the top surface of the support member has a length of about 14 to 19 mm.

6. The power toothbrush of claim 1 wherein a minor axis of the top surface of the support member has a width of about 12 to 15 mm.

7. A head for a power toothbrush comprising:
a support member configured for releasable attachment to a power toothbrush, the support member including a lower portion constructed to be rotationally oscillated, relative to a neck of the toothbrush, and a top surface having an elongated shape selected from the group consisting of oval, elliptical and rounded diamond, wherein the top surface of the support member has an overall surface area of from about 170 to 200 mm$^2$,
a plurality of tufts of bristles extending from the support member, and
a plurality of elastomeric fins pivotably mounted in and extending from the support member, each elastomeric fin having a textured surface.

8. The power toothbrush of claim 7 wherein the textured surface comprises ribs.

9. The power toothbrush of claim 7 wherein the tufts of bristles and elastomeric fins, in combination, have at least three different heights.

10. The power toothbrush of claim 7 wherein the tufts of bristles and elastomeric fins, in combination, and arranged so that their tips define a rounded contour.

11. The power toothbrush of claim 7 wherein a major axis of the top surface of the support member has a length of about 14 to 19 mm.

12. The power toothbrush of claim 7 wherein a minor axis of the top surface of the support member has a width of about 12 to 15 mm.

13. A head for a power toothbrush comprising:
a support member configured for releasable attachment to a power toothbrush, the support member including a lower portion constructed to be rotationally oscillated relative to a neck of the toothbrush, and a top surface having an elongated shape selected from the group consisting of oval, elliptical and rounded diamond, wherein the top surface of the support member has an overall surface area of from about 170 to 200 mm$^2$,
a plurality of tufts of bristles extending from the support member, and
a plurality of elastomeric fins pivotably mounted in and extending from the support member, each elastomeric fin having a textured surface comprising ribs,
wherein the tufts of bristles and elastomeric fins, in combination, have at least three different heights.

14. The power toothbrush of claim 13 wherein the tufts of bristles and elastomeric fins, in combination, and arranged so that their tips define a rounded contour.

15. The power toothbrush of claim 13 wherein a major axis of the top surface of the support member has a length of about 14 to 19 mm.

16. The power toothbrush of claim 15 wherein a minor axis of the top surface of the support member has a width of about 12 to 15 mm.

* * * * *